United States Patent [19]

Hung et al.

[11] Patent Number: 5,043,490

[45] Date of Patent: Aug. 27, 1991

[54] NOVEL FLUORINATED DIENES

[75] Inventors: Ming-Hong Hung; Aaron C. Su, both of Wilmington, Del.; Wei-Yuan Huang; Yuanfa Zhang, both of Shanghai, China

[73] Assignee: E. I. du Pont de Nemours and Company, Wilmington, Del.

[21] Appl. No.: 530,683

[22] Filed: May 30, 1990

[51] Int. Cl.[5] .................... C07C 21/18; C07C 17/28
[52] U.S. Cl. .................................. 570/128; 570/136; 570/158; 570/171
[58] Field of Search ................................ 570/136, 128

[56] References Cited

U.S. PATENT DOCUMENTS

| | | | |
|---|---|---|---|
| 2,874,166 | 2/1959 | Dixon | 570/128 |
| 4,839,390 | 6/1989 | Naumann et al. | 570/136 |
| 4,902,835 | 2/1990 | Kende et al. | 570/136 |

FOREIGN PATENT DOCUMENTS

| | | |
|---|---|---|
| 52-089603 | 7/1977 | Japan . |
| 142926 | 9/1982 | Japan ................................. 570/136 |
| 1-143840 | 6/1989 | Japan . |
| 1-168630 | 7/1989 | Japan . |

*Primary Examiner*—J. E. Evans
*Attorney, Agent, or Firm*—Paul R. Steyermark

[57] ABSTRACT

Novel 1,1,2-trifluorodienes, which have a minimum of seven carbon atoms and may contain in their molecule a phenylene or a methylphenylene moiety, are useful monomers, that can be polymerized in the presence of either free radical or coordination catalysts and can undergo selective reactions such, as for example, epoxidation of the vinyl (nonfluorinated) double bond. The resulting perfluorovinyl epoxy compounds also are useful monomers, which can undergo polymerization to useful materials.

6 Claims, No Drawings

NOVEL FLUORINATED DIENES

BACKGROUND OF THE INVENTION

This invention relates to certain novel fluorinated dienes, which are useful as polymerization monomers as well as the starting materials for making epoxides containing a fluorovinyl group, which also can be polymerized. Such epoxides are described in Ser. No. 07/530,376 of Ming H. Hung, which is being filed concurrently herewith.

Dienes, especially those having their double bonds in both terminal positions, are well known and many have found important industrial applications as polymerization monomers. These include, for example, 1,3-butadiene, 1,5-hexadiene, and 2-chloro-1,3-butadiene. Certain fluorinated dienes have been disclosed, for example, in Japanese Patent Applications Nos. 62-327712 (Publication No. 1-168630) of Central Glass K.K. and 62-301437 (Publication No. 1-143840) of Asahi Glass Co., Ltd.

Dienes that have a vinyl group at one end of the molecule and the perfluorovinyl group at the other end of the molecule can be expected to be able to undergo selective reactions, especially at the vinyl end of the molecule. This can lead to novel and interesting compounds, especially novel polymerization monomers, as shown in the above-cited patent application of Hung.

SUMMARY OF THE INVENTION

According to the present invention, there are now provided fluorinated dienes having the following formula (1)

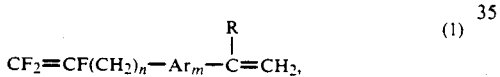

where m is 0 or 1; n is a positive integer of 2 to 10; R is hydrogen or methyl; and Ar is phenylene or methylphenylene;

with the provisos that,
when m is 0, n has a value of 3-10; and
when m is 1, n has the value of 2.

DETAILED DESCRIPTION OF THE INVENTION

The novel fluorinated dienes of the present invention are capable of both selective reactions and selective polymerization. As taught in the above-cited patent application of Hung, they can undergo selective epoxidation using a combination of fluorine, water, and acetonitrile. On the other hand, both ends of the molecule are capable of undergoing polymerization in the presence of free radicals, so that a free radical-initiated polymerization can be expected to result in a mixture of polymers resulting from the polymerization of either the vinyl group or the perfluorovinyl group, copolymers of both reacting species, and branched or crosslinked polymers resulting from secondary reactions of the pendant groups present on the polymers formed in the initial phase of polymerization. In the presence of coordination catalysts, however, only the vinyl group is capable of polymerizing, so that it is possible to prepare a well-defined polymer of the vinyl monomer and then cause it to undergo a desired amount of branching or crosslinking through its perfluorovinyl group.

These novel monomers will thus include, i.a., 1,1,2,-trifluoro-1,6-heptadiene; 1,1,2-trifluoro-1,7-octadiene;
1,1,2-trifluoro-1,8-nonadiene;
1,1,2-trifluoro-1,9-decadiene;
1,1,2-trifluoro-1,10-undecadiene;
1,1,2-trifluoro-1,11-dodecadiene;
1,1,2-trifluoro-6-methyl-1,6-heptadiene;
1,1,2-trifluoro-9-methyl-1,9-decadiene;
1-(3,4,4-trifluoro-3-butenyl)-4-vinylbenzene;
1-(3,4,4-trifluoro-3-butenyl)-2-methyl-4-vinylbenzene;
1-(3,4,4-trifluoro-3-butenyl)-3-methyl-4-vinylbenzene; and
1-(3,4,4-trifluoro-3-butenyl)-3-methyl-3-vinylbenzene.

Those monomers can be made by a series of reactions, most of which are generally known, although to the knowledge of the present inventors, they have never been combined and applied to the synthesis of monomers of this particular type.

The first step in the synthesis is the reaction of 1,2-dichloro-1,1,2-trifluoro-2-iodomethane (2) with a diene such as, e.g. 1,5-hexadiene (3) in the presence of sodium dithionite to give the corresponding 5-iodo-7,8-dichloro-7,8,8-trifluoro-1-octene (4). Iodine is replaced with hydrogen by means of zinc in ethanol, thus giving 7,8-dichloro-7,8,8-trifluoro-1-octene (5), which is dechlorinated with zinc in dimethyl sulfoxide (DMSO) to the desired diene, 1,1,2-trifluoro-1,7-octadiene (6).

This sequence of reactions is shown below:

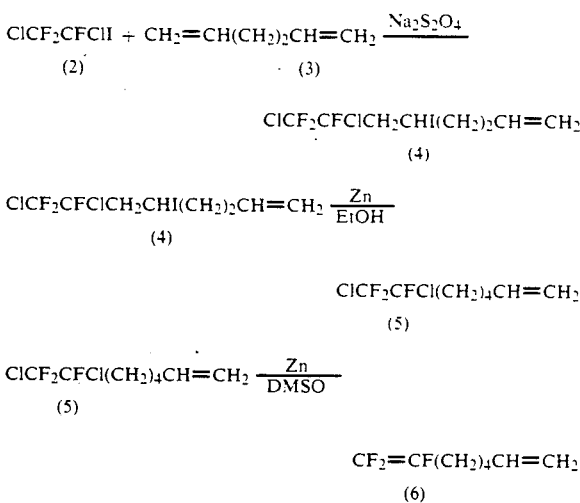

The synthesis of those monomers in which m = 1 is carried out in the same manner, except that, instead of the diene (2), one uses an aromatic divinyl compound; for example, 1,4-divinylbenzene (7) or a divinyltoluene, such as, for example, 1-methyl-2,5-divinylbenzene (8):

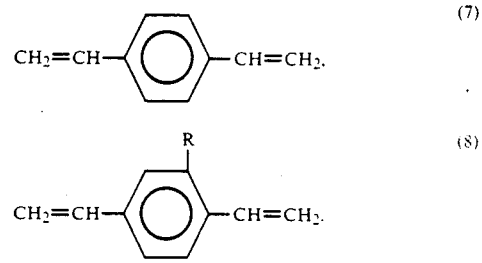

This invention is now illustrated by the following example of a representative embodiment thereof, where all parts, proportions and percentages are by weight unless otherwise indicated. All boiling points are reported uncorrected.

EXAMPLE

Preparation of 1,1,3-trifluoro-1,7-octadiene

Preparation of $ClCF_2CFClCH_2CHI(CH_2)_2CH=CH_2$

Ten grams (0.05 mole) of 88% $Na_2S_2O_4$, 3.7 g (0.05 mole) of $NaHCO_3$, 20 ml of acetonitrile, and 20 ml of water were mixed at 40° C. with stirring. A mixture of 56 g (0.2 mole) of $ClCF_2CFClI$ and 33 g (0.4 mole) of 1,5-hexadiene dissolved in each other was added gradually. When the first portion (about 10 ml) of the mixture was added, an exothermic reaction occurred. The temperature was maintained below 60° C. by controlling the rate of addition. Stirring was continued at 60° C. for 1 hour. After cooling, the organic layer was separated, and the low-boiling materials were removed. The desired product was obtained by distillation under reduced pressure. The yield of $ClCF_2CFClCH_2CHI(CH_2)_2CH=CH_2$, boiling at 124°-28° C. at a pressure of 4 kPa, was 35 g (48%). Fifteen grams of higher boiling residue remained in the distillation flask.

Preparation of $ClCF_2CFCl(CH_2)_4CH=CH_2$

A solution of 36 g (0.1 mole) of $ClCF_2CFClCH_2CHI(CH_2)_2CH=CH_2$ in 30 ml of absolute alcohol was added slowly to a suspension of 22 g (0.3 gramatom) of zinc in 50 ml of ethanol with stirring. An exothermic reaction occurred. Following the addition of the entire solution, the mixture was refluxed for 1 hour. After cooling, the supernatant liquid was poured into 200 ml of ice-cold dilute hydrochloric acid with vigorous stirring. The lower (organic) layer was separated and dried over anhydrous sodium sulfate. The reaction product was distilled at a reduced pressure; the main fraction, boiling at 88°-90° C. at a pressure of 2 kPa, was collected. The yield of $ClCF_2CFCl(CH_2)_4CH=CH_2$ was 14 g (59%).

Preparation of $CF_2=CF(CH_2)_4CH=CH_2$ $ClCF_2CFCl(CH_2)_4CH=CH_2$ (23.7 g, 0.1 mole), 19.5 g (0.3 gramatom) of zinc dust, and 50 ml of DMSO were introduced with stirring into a flask fitted with a short fractionation column. The contents were heated at 140°-180° C., and a distillate, boiling at 120°-40° C. was collected. The reaction was continued for about 4 hours, until no more product distilled. The product was washed with cold water, dried over anhydrous sodium sulfate, and purified by fractional distillation. The yield of $CF_2=CF(CH_2)_4CH=CH_2$, boiling at 118°-120° C. at a pressure of 102.6 kPa, was 11.0 g (66%).

In the same general manner was prepared 1,1,3-trifluoro-1,9-decadiene.

Both 1,1,3-trifluorodienes were characterized by their boiling points, nuclear magnetic resonance (NMR) spectra, and infrared (IR) spectra. These data are tabulated below. Proton NMR and $^{19}F$ NMR spectra were recorded at 60 MHz with a Varian EM-360 spectrometer. IR spectra were determined with a Zeiss Spectracord®, either as films or as KCl pellets.

TABLE

| Compound | b.p. (KPa) | $^1$HNMR ppm (TMS) in $CDCl_3$ | $^{19}$F NMR PPM (TMA) in $CDCl_3$ | IR (cm$^{-1}$) |
|---|---|---|---|---|
| $CF_2=CF(CH_2)_4CH=CH_2$ | 119-120 | 1.0-1.8 (M, 4H) | 29.5 (dd, 1F) | 1640 |
| | | 1.8-2.5 (m, 4H) | 48.6 (dd, 1F) | ($CH=CH_2$) |
| | | 4.8 (s, 1H) | 98.7 (dm, 1F) | 1794 |
| | | 5.0 (d, 1H) | | ($CF=CF_2$) |
| | | 5.68 (m, 1H) | | |
| $CF_2=CF(CH_2)_6CH=CH_2$ | 74-76 (5.3) | 0.8-1.8 (m, 8H) | 29.4 (dd, 1F) | 1640 |
| | | 1.8-2.5 (m, 4H) | 48.5 (dd, 1F) | ($CH=CH_2$) |
| | | 4.82 (m, 1H) | 97.5 (dm, 1F) | 1795 |
| | | 5.0 (dm, 1H) | | ($CF=CF_2$) |
| | | 5.7 (m, 1H) | | |

We claim:

1. A fluorinated diene having the following Formula (1):

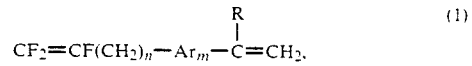

where m is 0 or 1; n is a positive integer of 2 to 10; R is hydrogen or methyl; and Ar is phenylene or methylphenylene;

with the provisos that,
when m is 0, n has a value of 3-10; and
when m is 1, n has the value of 2.

2. A fluorinated diene of claim 1 wherein m in Formula (1) is 0.

3. A fluorinated diene of claim 2 wherein n in Formula (1) is 4.

4. A fluorinated diene of claim 2 wherein n in Formula (1) is 6.

5. A fluorinated diene of claim 1 wherein m in Formula (1) is 1.

6. A fluorinated diene of claim 5, wherein Ar is 1,4-phenylene.

* * * * *